US00PP27370P3

(12) United States Plant Patent
Wood

(10) Patent No.: US PP27,370 P3
(45) Date of Patent: Nov. 15, 2016

(54) ***ABELIA* PLANT NAMED 'SMNAMDS'**

(50) Latin Name: *Abelia mosanensis*
Varietal Denomination: SMNAMDS

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 10 days.

(21) Appl. No.: 14/545,044

(22) Filed: Mar. 19, 2015

(65) Prior Publication Data

US 2016/0278260 P1 Sep. 22, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — C. A. Whealy

(57) ABSTRACT

A new and distinct cultivar of *Abelia* plant named 'SMNAMDS', characterized by its uniformly upright and rounded plant habit; freely branching habit; dense and bushy growth habit; freely and continuous flowering habit; dark reddish pink-colored flower buds; strongly fragrant flowers; and good garden performance.

1 Drawing Sheet

Botanical designation: *Abelia mosanensis.*
Cultivar denomination: 'SMNAMDS'.

BACKGROUND OF THE INVENTION

The present invention relates to a new and distinct cultivar of *Abelia* plant, botanically known as *Abelia mosanensis* and hereinafter referred to by the name 'SMNAMDS'.

The new *Abelia* is a product of a planned breeding program conducted by the Inventor in Grand Haven, Mich. The objective of the breeding program was to develop new compact and freely flowering *Abelia* plants with attractive flower coloration.

The new *Abelia* plant originated from an open-pollination in May, 2008 of an unnamed proprietary seedling selection of *Abelia mosanensis*, not patented, as the female, or seed parent with an unknown selection of *Abelia mosanensis*. The new *Abelia* plant was discovered and selected by the Inventor in May, 2012 as a single flowering plant within the progeny of the stated open-pollination in a controlled environment in Grand Haven, Mich.

Asexual reproduction of the new *Abelia* plant by softwood cuttings in a controlled greenhouse environment in Grand Haven, Mich. since May, 2012 has shown that the unique features of this new *Abelia* plant are stable and reproduced true to type in successive generations of asexual reproduction.

SUMMARY OF THE INVENTION

Plants of the new *Abelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNAMDS'. These characteristics in combination distinguish 'SMNAMDS' as a new and distinct *Abelia* plant:

1. Uniformly upright and rounded plant habit.
2. Freely branching habit; dense and bushy growth habit.
3. Freely and continuous flowering habit.
4. Dark reddish pink-colored flower buds.
5. Strongly fragrant flowers; fragrance is pleasant.
6. Good garden performance.

Plants of the new *Abelia* can be compared to plants of the female parent selection. In side-by-side comparisons, plants of the new *Abelia* differ primarily from plants of the female parent selection in the following characteristics:

1. Plants of the new *Abelia* are more uniform than plants of the female parent selection.
2. Plants of the new *Abelia* have darker-colored flower buds than plants of the female parent selection.
3. Flowers of plants of the new *Abelia* are more fragrant than flowers of plants of the female parent selection.

Plants of the new *Abelia* can be compared to plants of other unnamed selections of *Abelia mosanensis* known to the Inventor, not patented. In side-by-side comparisons plants of the new *Abelia* differed from plants of other unnamed selections of *Abelia mosanensis* known to the Inventor in the following characteristics:

1. Plants of the new *Abelia* were more uniform than plants of other unnamed selections of *Abelia mosanensis* known to the Inventor.
2. Plants of the new *Abelia* had darker-colored flower buds than plants of other unnamed selections of *Abelia mosanensis* known to the Inventor.
3. Flowers of plants of the new *Abelia* were more fragrant than flowers of plants of other unnamed selections of *Abelia mosanensis* known to the Inventor.

BRIEF DESCRIPTION OF THE PHOTOGRAPH

The accompanying colored photograph illustrates the overall appearance of the new *Abelia* plant showing the colors as true as it is reasonably possible to obtain in colored reproductions of this type. Colors in the photograph may differ slightly from the color values cited in the detailed botanical description which accurately describe the colors of the new *Abelia* plant.

The photograph is a close-up view of a typical flowering plant of 'SMNAMDS'.

DETAILED BOTANICAL DESCRIPTION

The aforementioned photograph and following observations, measurements and values describe plants grown during the late spring in one-gallon containers in a polypropylene-covered shadehouse in Grand Haven, Mich. and under cultural practices typical of commercial *Abelia* production. During the production of the plants, day temperatures ranged from 18° C. to 27° C. and night temperatures ranged from 5° C. to 10° C. Plants were two years old when the photograph and the description were taken. In the description, color references are made to The Royal Horticultural Society Colour Chart, 1995 Edition, except where general terms of ordinary dictionary significance are used.

Botanical classification: *Abelia mosanensis* 'SMNAMDS'.

Parentage:

- *Female, or seed, parent*.—Unnamed proprietary seedling selection of *Abelia mosanensis*, not patented.
- *Male, or pollen, parent*.—Unknown selection of *Abelia mosanensis*, not patented.

Propagation:

- *Type*.—By softwood cuttings.
- *Time to initiate roots, summer*.—About 18 days at temperatures about 27° C.
- *Time to produce a rooted young plant, summer*.—About 40 days at temperatures about 27° C.
- *Root description*.—Medium in thickness; creamy white to brown in color.
- *Rooting habit*.—Moderate to freely branching; medium density.

Plant description:

- *Plant form and growth habit*.—Perennial shrub; uniformly upright and rounded plant habit; vigorous growth habit.
- *Branching habit*.—Freely branching habit, dense and bushy growth habit with about 15 lateral branches developing per plant; pinching enhances lateral branch development.
- *Plant height*.—About 30 cm.
- *Plant diameter* (*area of spread*).—About 45 cm.

Lateral branch description:

- *Length*.—About 25 cm.
- *Diameter*.—About 3 mm.
- *Internode length*.—About 3 cm to 4.5 cm.
- *Aspect*.—Upright to outwardly.
- *Texture, developing*.—Slightly pubescent.
- *Texture, fully developed*.—Woody.
- *Color, developing*.—Upper surface, close to 178B; lower surface, close to 144B.
- *Color, fully developed*.—Close to 197B.

Leaf description:

- *Arrangement*.—Opposite, simple.
- *Length*.—About 6.5 cm to 7.3 cm.
- *Width*.—About 2.3 cm.
- *Shape*.—Lanceolate.
- *Apex*.—Acuminate.
- *Base*.—Attenuate.
- *Margin*.—Entire.
- *Texture, upper and lower surfaces*.—Pubescent.
- *Venation pattern*.—Pinnate.
- *Color*.—Developing leaves, upper surface: Close to 141B. Developing leaves, lower surface: Close to 143C. Fully expanded leaves, upper surface: Close to 141A; venation, close to 141A. Fully expanded leaves, lower surface: Close to 138B; venation, close to 138B.
- *Petioles*.—Length: About 5 mm. Diameter: About 1.5 mm. Texture, upper and lower surfaces: Pubescent. Color, upper surface: Close to 141A. Color, lower surface: Close to 138B.

Flower description:

- *Flower appearance and arrangement*.—Single funnel-form flowers arranged on terminal panicles; freely flowering habit with about six flowers per inflorescence and about 35 to 40 flowers developing per plant; flower face upright to outwardly.
- *Inflorescence height*.—About 2.8 cm.
- *Inflorescence width*.—About 5 cm.
- *Fragrance*.—Strongly fragrant, pleasant.
- *Natural flowering season*.—Plants begin flowering in early spring in Michigan; flowers not persistent.
- *Flower diameter*.—About 1.5 cm.
- *Flower depth*.—About 1.7 cm.
- *Flower buds*.—Length: About 1.9 cm. Diameter: Towards the apex, about 5 mm; towards the base, about 1 mm. Shape: Lanceolate to spatulate. Color: Towards the apex, close to 57A; towards the base, close to 1C.
- *Petals*.—Quantity and arrangement: Five fused petals arranged in a single whorl; petals slightly recurved. Lobe length: About 7 mm. Lobe width: About 5 mm. Shape: Elliptic to obovate. Apex: Obtuse; slightly recurved. Base: Obtuse, fused. Margin: Entire. Texture, upper and lower surfaces: Smooth, glabrous; thick and fleshy. Color: When opening, upper surface: Close to 155D; towards the apex, close to 65D. When opening, lower surface: Close to 155D; towards the apex, close to 62B. Fully opened, upper surface: Close to 155D. Fully opened, lower surface: Close to 155D; towards the apex, close to 63C.
- *Sepals*.—Quantity and arrangement: Five fused sepals arranged in a single whorl. Length: About 9 mm. Width: About 3 mm. Shape: Lanceolate to oblanceolate. Apex: Acute. Base: Cuneate. Margin: Entire. Texture, upper and lower surfaces: Smooth, glabrous; along the margins, pubescent. Color, upper surface: Close to 182A. Color, lower surface: Close to 146D.
- *Peduncles*.—Length: About 5 cm. Diameter: About 1 mm. Strength: Strong. Texture: Pubescent. Angle: Upright to outwardly. Color: Close to 144B.
- *Pedicels*.—Length: About 5 mm. Diameter: About 2 mm. Strength: Strong. Texture: Pubescent. Angle: Upright to outwardly. Color: Close to 144B.
- *Reproductive organs*.—Stamens: Quantity per flower: Five. Filament length: About 1 mm. Filament color: Close to 155D. Anther length: About 1 mm. Anther shape: Oblong. Anther color: Close to 155C. Pollen amount: Scarce. Pollen color: Close to 155C. Pistils: Quantity per flower: One. Pistil length: About 1.5 cm. Stigma shape: Globular. Stigma color: Close to 134A. Style length: About 1.5 cm. Style color: Close to 155C. Ovary color: Close to 144B.

*Seeds and fruits*.—Seed and fruit production have not been observed on plants of the new *Abelia*.

Garden performance: Plants of the new *Abelia* have been observed to have good garden performance and to tolerate rain, wind and temperatures ranging from about −27 C to about 35 C.

Pathogen & pest resistance: Plants of the new *Abelia* have not been shown to be resistant to pathogens and pests common to *Abelia* plants.

It is claimed:

1. A new and distinct *Abelia* plant named 'SMNAMDS' as illustrated and described.

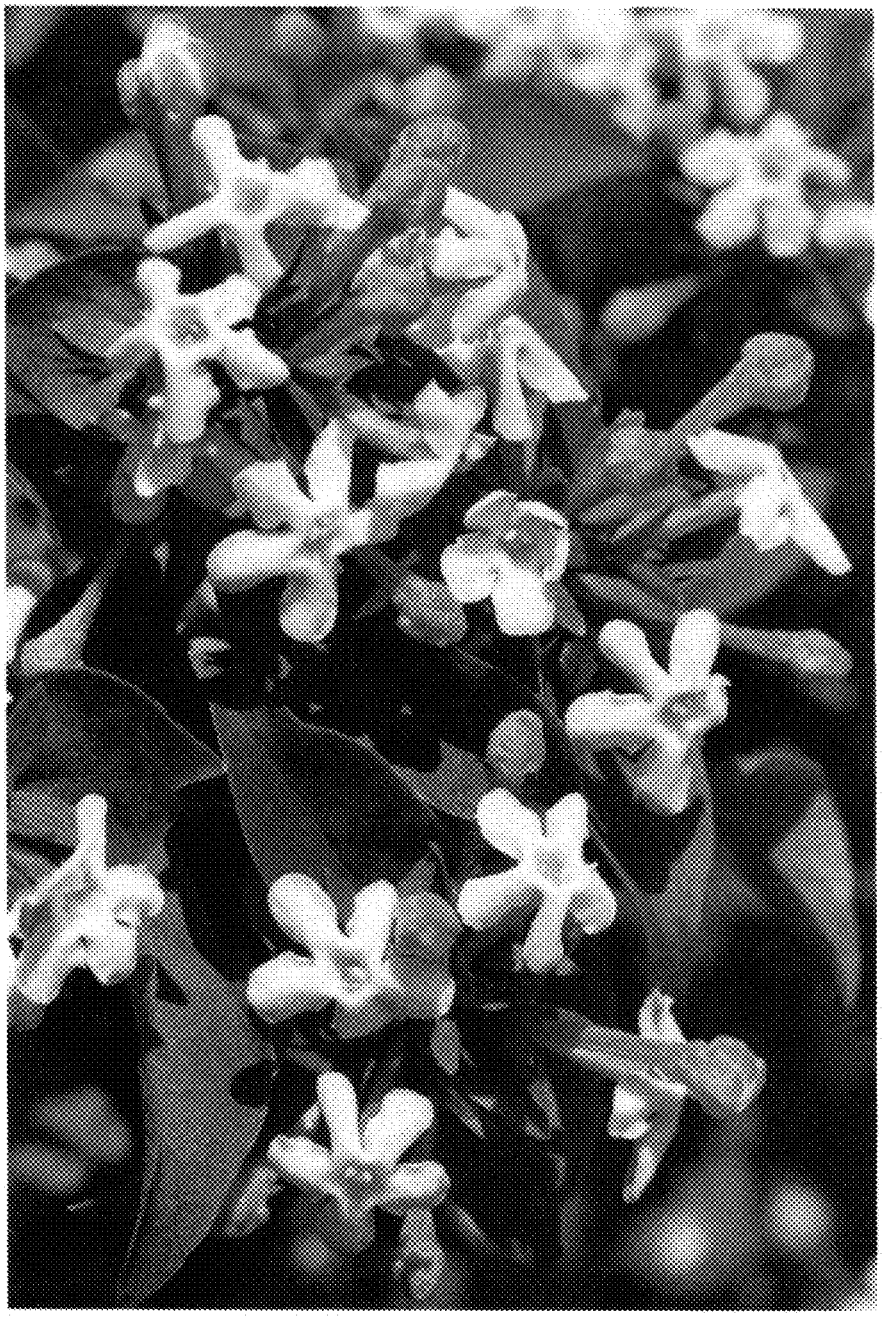

* * * * *